United States Patent [19]

Hustead et al.

[11] Patent Number: 4,938,970

[45] Date of Patent: Jul. 3, 1990

[54] PAINLESS ELECTROLYTE SOLUTIONS

[76] Inventors: Robert E. Hustead, 2401 N. Pershing, Wichita, Kans. 67220; David R. Hustead, 3201 41st St., Sioux City, Iowa 51108

[21] Appl. No.: 74,806

[22] Filed: Jul. 17, 1987

Related U.S. Application Data

[63] Continuation-in-part of Ser. No. 11,809, Feb. 6, 1987.

[51] Int. Cl.$^5$ .............................................. A61K 33/14
[52] U.S. Cl. ................................... 424/678; 424/677; 424/679; 424/680; 424/681; 424/722
[58] Field of Search ............... 424/153, DIG. 13, 677, 424/678, 679, 680, 681, 722, 506

[56] References Cited

U.S. PATENT DOCUMENTS

| | | | |
|---|---|---|---|
| 3,993,750 | 11/1976 | Fox | 424/680 |
| 4,180,588 | 12/1979 | Mori | 514/563 |
| 4,256,766 | 3/1981 | Mori | 514/563 |
| 4,339,452 | 7/1982 | Hard | 514/249 |
| 4,440,788 | 4/1984 | Terayama | 514/893 |
| 4,443,432 | 4/1984 | Garabedian | 424/127 |
| 4,550,022 | 10/1985 | Garabedian | 424/153 X |
| 4,663,166 | 5/1987 | Veech | 424/146 |
| 4,663,289 | 5/1987 | Veech | 424/153 X |
| 4,837,021 | 6/1989 | Andermann | 424/681 |

FOREIGN PATENT DOCUMENTS

| | | | |
|---|---|---|---|
| 2550946 | 3/1985 | France | 424/153 |
| 0980719 | 12/1982 | U.S.S.R. | 424/153 |
| 2064320 | 6/1981 | United Kingdom | 424/153 |

OTHER PUBLICATIONS

Wightman, M. A. et al., *Anesthesiology* 45: 786–789 (1976).
Craig, D. et al., *Anesth. Analg.* 56: 219–221 (1977).
Bloom, L. H. et al., *Opthalmic. Surg.* 15: 603 (1984).
Hallen, B. et al., *Anesthesia* 39: 969–972 (1984).
Hallen B. et al., *Anesthesiology* 57: 340–343 (1982).
Harper, J. K. et al., *Am. J. Opthalmol.* 45: 269–276 (1958).
Merrill, D. L. et al., *Am. J. Opthalmol.* 49:895–898 (1960).
Edelhauser, H. et al., *Arch. Opthalmol.* 93:648–657 (1975).
Edelhauser, H. et al., *Arch. Opthalmol.* 96:516–520 (1978).
Edelhauser, H. et al., *Amer. J. Opthalmol.* 81:473–481 (1976).
Thomas, D. V., *Anesth. Analg.*, 63:883 (1984).
Christiansen, J. M. et al., *Amer. J. Opthalmol.* 82:594–597 (1976).
Maurice, D. M. et al., *Amer. J. Opthalmol.* 99:691–696 (1985).
Thomas, D. V., *Anesthesia Intensive Care* 13:101 (1984).
Kramer, R. M. *Survey of Opthalmology* 30:102–110 (1985).
Svendsen, O., *Acta Pharmacol. et. Toxicol.* 55:422–424 (1984).
Myers, R. R. et al., *Anesthesiology* 64:29–35 (1986).
Foster, B. S. et al., *Anesth. Analg.* 58:727–736 (1980).
Yagiela, J. A. et al., *Anesth. Analg.* 60:471–480 (1981).
Fox, C. L. et al., *J.A.M.A.* 148:827–833 (1952).
Masterton and Slowinski, *Chemical Principles*, W. B. Saunders Co., 4th Edition pp. 481–485 (1973).

*Primary Examiner*—William R. Dixon, Jr.
*Assistant Examiner*—James M. Hunter, Jr.
*Attorney, Agent, or Firm*—Saidman, Sterne, Kessler & Goldstein

[57] ABSTRACT

This invention relates to compositions comprising electrolytes dissolved in a buffer which is painless when administered by irrigation.

This invention also relates to compositions comprising a local anesthetic such as lidocaine, procaine, mepivacaine or marcaine, dissolved in a buffered solution containing salts which do not cause pain when the solutions are administered. The compositions are useful for administration as painless local anesthetics and painless irrigation-anesthetizing solutions for human and animal use. The invention further relates to methods for painless irrigation of wounds and of inducing painless local anesthesia comprising administering an effective amount of the compositions of this invention to an animal.

11 Claims, No Drawings

PAINLESS ELECTROLYTE SOLUTIONS

CROSS REFERENCE TO RELATED APPLICATIONS

This application is continuation-in-part of application Ser. No. 011,809, filed in the United States Patent and Trademark Office on Feb. 6, 1987.

FIELD OF THE INVENTION

This invention relates to painless solutions and compositions comprising a local anesthetic such as lidocaine, procaine, chloroprocaine, proparacaine, mepivacaine, bupivacaine, dissolved in a buffered solution containing salts in concentrations which do not cause pain when the solutions are injected or applied to the cornea. The compositions are useful for administration as painless local anesthetics and painless irrigation-anesthetizing solutions for human and animal use. The invention further relates to a method of inducing painless local anesthesia comprising administering an effective amount of the compositions of this invention to an animal.

BACKGROUND OF THE INVENTION

Local anesthetics, when injected as a solution in normal saline, in general cause pain. Wightman, M. A. et al., *Anesthesiology* 45:687-689 (1976). In addition, all topical anesthetic preparations sting when applied to the cornea. Some anesthetics were shown to cause less pain than others. These authors provided a method to measure the pain of local anesthetic injection. They reported the first modern painless local anesthetic, bacteriostatic saline, which comprises 0.9% benzyl alcohol in normal saline. They reported bacteriostatic saline painlessly produces mild skin anesthesia after intradermal injection. However, the anesthesia was not profound and lasted for only 10-15 minutes. This was long enough to start an I.V., but not long enough to keep the site from hurting. However, use of solutions containing benzyl alcohol are not preferred because benzyl alcohol is cytotoxic and has been cited as playing a possible role in flaccid paraparesis following obstetric epidural anesthesia. Douglas, C. et al., *Anesth. Analg.* 56:219-22 (1977). Other disadvantages of benzyl alcohol containing solutions are that they sting when applied to the cornea and are ineffective as a topical anesthetic.

Other workers have reported that the warming of local anesthetic agents prior to administration helps to decrease the discomfort associated with injection. Bloom, L. H. et al., *Opthalmic. Surg.* 15:603 (1984). Traditional methods of decreasing the pain of the injection of local anesthetics include hypnosis (suggestion) and sedatives (amnesia producing drugs). Still other workers have reported application of a local anesthetic cream to decrease the pain of injection. Hallen, B. et al., *Anesthesia* 39:969-972 (1984); Hallen et al., *Anesthesiology* 57:340-342 (1982).

The pain of injection around and behind the eye can cause cardiac arrest, induce angina, incite asthma, and cause nausea and vomiting. The use of sedatives to ward off these problems has played a key role in anesthesia safety. However, stimuli from injection can cause an untoward response despite high doses of sedatives. In addition, sedatives can have undesirable side effects once the pain of injection is gone. These include disorientation and difficulty in establishing the success of a nerve block. Residual sedation can interfere with the safe ambulation of the elderly. Thus, patient safety is best served by avoiding pain. In addition, patients will be better served if the pain of injection of local anesthetics is reduced.

Thus, a need exists for compositions and methods for administering local anesthetics which do not cause pain. In addition, a need exists for solutions which may be used to irrigate wounds, abrasions, lacerations, and burns without pain.

SUMMARY OF THE INVENTION

This invention relates to painless solutions which may be used for irrigation of wounds, abrasions, and burns, comprising:

(a) electrolytes, present at a concentration where they do not cause pain; and (b) a buffered solution of pH 6.85-8.0.

This invention also relates to methods and compositions for the administration of painless local anesthetic compositions comprising one or more local anesthetics dissolved in the painless solutions. The invention further relates as well to methods of painless irrigation and of inducing painless anesthesia by administering the compositions of this invention.

Administration of the anesthetic compositions of this invention avoids the use of general anesthesia to perform surgery and the inherent dangers of this procedure. In addition, administration of these compositions allow patients to be anesthetized in state of consciousness so that they may cooperate with the surgeon.

Further, the compositions of this invention are safer to tissues, less irritating, have a lower effective concentration of anesthetic, are less neurotoxic, less myotoxic, and suitable for topical administration or by injection.

DESCRIPTION OF THE PREFERRED EMBODIMENT

By the term "local anesthetic" is intended all such compounds which may be administered to achieve local anesthesia. See Remington's Pharmaceutical Sciences. Mac Publishing Co., Easton, PA, A. Osol, Ed. (1980, p. 991-1003). Preferred anesthestics include procaine, chloroprocaine, lidocaine, mepivacaine, bupivacaine and proparacaine.

By the term "animal" is intended all animals which derive benefit from the painless local anesthetic compositions of this invention. Foremost among such animals are humans; however, the invention is not intended to be so limiting, it being within the contemplation of the invention to treat any and all such animals which may experience the beneficial effects of the invention.

By the term "painless electrolytes" is intended electrolytes which do not cause pain when administered to an animal as part of a buffered solution, iso-osmotic to tissue fluid, wherein said electrolytes are present at concentrations which do not cause pain. Such electrolytes include, but are not limited to, $H^+$, $K^+$, $Ca^{++}$, and $Mg^{++}$ and $Na^+$ salts of painless anions.

By the term "painless anions" is intended negatively charged counter ions which do not cause pain when injected as part of a buffered solution which contains a local anesthetic. Foremost among such counter ions are chloride and acetate. However, it is intended that all such counter ions are within the scope of this invention.

Incorporation of these electrolytes in painless concentrations serves not only to prevent the pain which occurs from injection, but also renders the dissolved anesthetic more effective in potency than if said electrolytes were not present.

The compositions of the present invention, in and of themselves, find utility for induction of painless local anesthesia. Thus, intradermal injection of these painless anesthetics produces mild anesthesia and allows subsequent injection of standard local anesthetics without the pain these anesthetics normally cause. These painless solutions may also be applied as topical aesthetics or dilute local anesthetics before administration of an "eye block" prior to eye surgery. These compositions may be applied as irrigation solutions or by injection.

It has been found that the pH and the type and concentration of electrolytes present in a solution is critical as to whether the resulting solution will be painless upon administration. In particular, electrolytes which are normally present in tissue fluid, and which are therefore painless, include $H^+$, $Na^+$, $K^+$, $Ca^{++}$ and $Mg^{++}$ salts of painless anions. Preferred painless anions comprise chloride and acetate. Thus, the anesthetic may be dissolved in a solution containing acetic acid and back titrated with aqueous sodium hydroxide to give a stable pH of 6.85 to 8.0. Alternatively, the anesthetic may be dissolved in aqueous HCl and titrated with aqueous sodium acetate to give the requisite pH of 6.85–8.0. The cations are then added as chloride or acetate salts to give a solution which is adjusted in concentration to be painless and iso-osmotic with tissue fluid. The range of such concentrations which give rise to a painless local anesthetic appear in Table I.

TABLE I

| | Concentration (meq/L) |
|---|---|
| $Na^+$ | 110–150 |
| $Cl^-$ | 80–125 |
| $K^+$ | 2–10 |
| $Ca^{++}$ | 0–3 |
| $Mg^{++}$ | 1–5 |

A typical dosage comprises 0.25 to 5% of a local anesthetic such as lidocaine hydrochloride, 0.5–10 meq/L of $K^+$, 1–10 meq/L of $Ca^{++}$, and 1–5 meq/L of $Mg^{++}$, 120–140 meq/L $Na^+$ and 80–125 meq/L $Cl^-$. The pH of this solution is 6.85–8.0.

A preferred embodiment of this invention comprises dissolution of the local anesthetic in aqueous acetic acid followed by back titration with aqueous sodium hydroxide to a pH=6.85–8.0 and dilution of this solution to a concentration of 2% lidocaine hydrochloride, 110–150 meq/L $Na^+$ and 80–125 meq/L $Cl^-$. Preferred concentrations of other electrolytes are 1 meq/L for $K^+$, 5 meq/L for $Ca^{++}$, and 3 meq/L for $Mg^{++}$.

When these painless anesthetics are injected, additional methods are used to further reduce the pain associated with injection. These methods include use of a small needle (30 or 27 gauge) and slow hydraulic infiltration of solutions at skin temperature. Compositions of this invention do not sting when applied to the cornea.

Painless solutions may also be prepared for irrigation of wounds, lacerations, abrasions, or burns which comprise the electrolytes listed in Table 1 in a solution of pH 6.85–8.0. Such a solution may be prepared by dissolving the electrolytes in Table I, as their chloride or acetate salts, in a buffer sodium acetate-acetic acid buffer solution of pH 6.85–8.0.

Having now fully described the invention, it will be appreciated by those skilled in the art that the same can be performed with a wide range of equivalent parameters of composition, conditions and mode of administration without departing from the spirit or scope of the invention or any embodiment thereof.

What is claimed is:

1. A composition consisting of:
   (a) electrolytes selected from the group consisting of $K^+$, $Ca^{++}$, $Na^+$ and $Mg^{++}$ salts of anions, wherein said $K^+$ is present at a concentration of 2–10 meq/L, said $Ca^{++}$ is present at a concentration of 0–3 meq/L, said $Mg^{++}$ is present at a concentration of 1–5 meq/L, and said $Na^+$ is present at a concentration of 110–150 meq/L; and
   (b) a solution of pH 6.85–8.0;
   wherein said composition is painless when administered internally, ophthalmically or by irrigation of a wound, abrasion, laceration or burn, and wherein said solution is obtained by titrating aqueous acetic acid to pH 6.85–8.0 with aqueous sodium hydroxide and diluting to a final concentration of 110–150 meq/L $Na^+$ and 80–125 meq/L $Cl^-$ or by titrating aqueous HCl to a pH of 6.85–8.0 with aqueous sodium acetate and diluting to a concentration of 110–150 meq/L $Na^+$ and 80–125 meq/L $Cl^-$.

2. A composition comprising:
   (a) electrolytes selected from the group consisting of $K^+$, $Ca^{++}$, $Na^+$ and $Mg^{++}$ salts of anions, wherein said $K^+$ is present at a concentration of 2–10 meq/L, said $Ca^{++}$ is present at a concentration of 0–3 meq/L, said $Mg^{++}$ is present at a concentration of 1–5 meq/L, and said $Na^+$ is present at a concentration of 110–150 meq/L; and
   (b) a solution of pH 6.85–8.0;
   (c) one or more local anesthetics wherein said composition is painless when administered internally, ophthalmically or by irrigation of a wound, abrasion, laceration or burn.

3. The composition of claim 2, wherein said local anesthetic is selected from the group consisting of lidocaine, mepivacaine, bupivacaine, chloroprocaine, procaine, and proparacaine.

4. The composition of claim 2, wherein the local anesthetic is a combination of anesthetics comprising mepivacaine and bupivacaine.

5. A method for providing painless irrigation of a wound, abrasion, laceration or burn, comprising irrigation with a composition consisting of:
   (a) electrolytes selected from the group consisting of $K^+$, $Ca^{++}$, $Na^+$ and $Mg^{++}$ salts of anions, wherein said $K^+$ is present at a concentration of 2–10 meq/L, said $Ca^{++}$ is present at a concentration of 0–3 meq/L, said $Mg^{++}$ is present at a concentration of 1–5 meq/L, and said $Na^+$ is present at a concentration of 110–150 meq/L; and
   (b) a solution of pH 6.85–8.0;
   wherein said composition is painless when administered internally, ophthalmically or by irrigation of a wound, abrasion, laceration or burn, and wherein said solution is obtained by titrating aqueous acetic acid to pH 6.85–8.0 with aqueous sodium hydroxide and diluting to a final concentration of 110–150 meq/L $Na^+$ and 80–125 meq/L $Cl^-$ or by titrating aqueous HCl to a pH of 6.85–8.0 with aqueous sodium acetate and diluting to a concentration of 110–150 meq/L $Na^+$ and 80–125 meq/L $Cl^-$.

6. A method for inducing painless anesthesia comprising administering to an animal a composition comprising:

(a) electrolytes selected from the group consisting of $K^+$, $Ca^{++}$, $Na^+$ and $Mg^{++}$ salts of anions, wherein said $K^+$ is present at a concentration of 2–10 meq/L, said $Ca^{++}$ is present at a concentration of 0–3 meq/L, said $Mg^{++}$ is present at a concentration of 1–5 meq/L, and said $Na^+$ is present at a concentration of 110–150 meq/L;

(b) a solution of pH 6.85–8.0; and (c) one or more local anesthetics;

wherein said composition is painless when administered internally, ophthalmically or by irrigation of a wound, abrasion, laceration or burn.

7. The method of claim 6, wherein said administration is by injection.

8. The method of claim 6, wherein said administration is by irrigation.

9. The method of claim 6, 7 or 8 wherein said animal is a human.

10. The method of claim 6, wherein said local anesthetic is selected from the group consisting of lidocaine, mepivacaine, bupivacaine, chloroprocaine, procaine and proparacaine.

11. The method of claim 6, wherein the local anesthetic is a combination of anesthetics comprising mepivacaine and bupivacaine.

* * * * *

UNITED STATES PATENT AND TRADEMARK OFFICE
CERTIFICATE OF CORRECTION

PATENT NO. : 4,938,970

DATED : July 3, 1990

INVENTOR(S) : Robert F. Hustead and David R. Hustead

It is certified that error appears in the above-identified patent and that said Letters Patent is hereby corrected as shown below:

On the first page of the Patent, the inventor's name "Robert E. Hustead" should read --Robert F. Hustead--.

Signed and Sealed this

Seventeenth Day of December, 1991

Attest:

HARRY F. MANBECK, JR.

Attesting Officer     Commissioner of Patents and Trademarks